US006492425B1

(12) United States Patent
Callahan et al.

(10) Patent No.: US 6,492,425 B1
(45) Date of Patent: Dec. 10, 2002

(54) INHIBITORS OF TRANSCRIPTION FACTOR-NF-κB

(75) Inventors: James F. Callahan, Philadelphia, PA (US); Marie C. Chabot-Fletcher, Phoenixville, PA (US)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 09/720,018

(22) PCT Filed: Jun. 18, 1999

(86) PCT No.: PCT/US99/13652

§ 371 (c)(1),
(2), (4) Date: Dec. 19, 2000

(87) PCT Pub. No.: WO99/65449

PCT Pub. Date: Dec. 23, 1999

Related U.S. Application Data

(60) Provisional application No. 60/089,827, filed on Jun. 19, 1998.

(51) Int. Cl.[7] ............................................. A61K 31/165
(52) U.S. Cl. ........................................................ 514/622
(58) Field of Search .......................................... 514/622

(56) References Cited

U.S. PATENT DOCUMENTS 4,803,279 A 2/1989 Bender et al. ............... 546/271

FOREIGN PATENT DOCUMENTS

| WO | WO 92/03451 | | 3/1992 |
| WO | WO92/20795 | * | 11/1992 |
| WO | WO94/28887 | * | 12/1994 |
| WO | WO99/07382 | * | 2/1999 |

OTHER PUBLICATIONS

Maury, et al., "Mobile Keto Allyl Systems. Vi[a]. Reaction of 3–Bromo–2–benzal–1–indanone with Amines", Journal of Organic Chemistry, (1968), 33(5), pp. 1900–1907.

Pearson, et al., "Elimination Reactions of α–Halogenated Ketones. IX.[1a] A Comparison of the Reactions of 2–Bromo–20(α–bromobenzyl)–1–indanone with Those of 2–Bromo–2–(α–bromobenzyl)–3, 3–dimethyl–1–indanone", (1962), 27, pp. 3038–3044.

Hassner, et al., "The Chemistry of Derivatives of 2–Benzaltetralone. II. Absorption Spectra and Stereostructure", (1958), J. Amer. Chem. Society, 80, pp. 893–901.

Clark, et al., "5–(Alkylsulfonyl)salicylanilides as Potential Dental Antiplaque Agents", (1986), J. Med. Chem., 29, pp. 25–29.

* cited by examiner

*Primary Examiner*—Russell Travers
*Assistant Examiner*—San-ming Hui
(74) *Attorney, Agent, or Firm*—Soma G. Simon; Mary E. McCarthy; Charles M. Kinzig

(57) ABSTRACT

The present invention provides pharmaceutical compositions of salicylanilide inhibitors of transcription factor NF-κB, and methods for treating diseases in which activation of NF-κB is implicated. More specifically, the present invention provides methods of treatment of a variety of diseases associated with NF-κB activation including inflammatory disorders; particularly rheumatoid arthritis, inflammatory bowel disease, and asthma; dermatosis, including psoriasis and atopic dermatitis; autoimmune diseases; tissue and organ rejection; Alzheimer's disease; stroke; atherosclerosis; restenosis; cancer, including Hodgkin's disease; certain viral infections, including AIDS; osteoarthritis; osteoporosis; and Ataxia Telangiestasia by administering to a patient in need thereof a compound of the present invention.

4 Claims, No Drawings

INHIBITORS OF TRANSCRIPTION FACTOR-NF-κB

The application claims the benefit of a U.S. provisional application No. 60/089,827, filed Jun. 19, 1998.

FIELD OF THE INVENTION

This invention relates in general to salicylanilide inhibitors of transcription factor NF-κB. Such compounds are particularly useful for treating diseases in which activation of NF-κB is implicated. More specifically, these compounds inhibit IκB phosphorylation and subsequent degradation. Such compounds are useful in the treatment of a variety of diseases associated with NF-κB activation including inflammatory disorders; particularly rheumatoid arthritis, inflammatory bowel disease, and asthma; dermatosis, including psoriasis and atopic dermatitis; autoimmune diseases; tissue and organ rejection; Alzheimer's disease; stroke; atherosclerosis; restenosis; cancer, including Hodgkins disease; and certain viral infections, including AIDS; osteoarthritis; osteoporosis; and Ataxia Telangiestasia.

BACKGROUND OF THE INVENTION

Recent advances in scientific understanding of the mediators involved in acute and chronic inflammatory diseases and cancer have led to new strategies in the search for effective therapeutics. Traditional approaches include direct target intervention such as the use of specific antibodies, receptor antagonists, or enzyme inhibitors. Recent breakthroughs in the elucidation of regulatory mechanisms involved in the transcription and translation of a variety of mediators have led to increased interest in therapeutic approaches directed at the level of gene transcription.

NF-κB belongs to a family of closely related dimeric transcription factor complexes composed of various combinations of the Rel/NF-κB family of polypeptides. The family consists of five individual gene products in mammals, RelA (p65), NF-κB1 (p50/p105), NF-κB2 (p49/p100), c-Rel, and RelB, all of which can form hetero- or homodimers. These proteins share a highly homologous 300 amino acid "Rel homology domain" which contains the DNA binding and dimerization domains. At the extreme C-terminus of the Rel homology domain is a nuclear translocation sequence important in the transport of NF-κB from the cytoplasm to the nucleus. In addition, p65 and cRel possess potent transactivation domains at their C-terminal ends.

The activity of NF-κB is regulated by its interaction with a member of the inhibitor IκB family of proteins. This interaction effectively blocks the nuclear localization sequence on the NF-κB proteins, thus preventing-migration-of the dimer to the nucleus. A wide variety of stimuli activate NF-κB through what are likely to be multiple signal transduction pathways. Included are bacterial products (LPS), some viruses (HIV-1, HTLV-1), inflammatory cytokines (TNFα, IL-1), and environmental stress. Apparently common to all stimuli however, is the phosphorylation and subsequent degradation of IκB. IκB is phosphorylated on two N-terminal serines by the recently identified IκB kinases (IKK-α and IKK-β). Site-directed mutagenesis studies indicate that these phosphorylations are critical for the subsequent activation of NF-κB in that once phosphorylated the protein is flagged for degradation via the ubiquitin-proteasome pathway. Free from IκB, the active NF-κB complexes are able to translocate to the nucleus where they bind in a selective manner to preferred gene-specific enhancer sequences. Included in the genes regulated by NF-κB are a number of cytokines, cell adhesion molecules, and acute phase proteins.

It is well-known that NF-κB plays a key role in the regulated expression of a large number of pro-inflammatory mediators including cytokines such as IL-6 and IL-8. Cell adhesion molecules, such as ICAM and VCAM, and inducible nitric oxide synthase (iNOS). Such mediators are known to play a role in the recruitment of leukocytes at sites of inflammation and in the case of iNOS, may lead to organ destruction in some inflammatory and autoimmune diseases.

The importance of NF-κB in inflammatory disorders is further strengthened by studies of airway inflammation including asthma, in which NF-κB has been shown to be activated. This activation may underlie the increased cytokine production and leukocyte infiltration characteristic of these disorders. In addition, inhaled steroids are known to reduce airway hyperresponsiveness and suppress the inflammatory response in asthmatic airways. In light of the recent findings with regard to glucocorticoid inhibition of NFκB, one may speculate that these effects are mediated through an inhibition of NFκB.

Further evidence for a role of NF-κB in inflammatory disorders comes from studies of rheumatoid synovium. Although NF-κB is normally present as an inactive cytoplasmic complex, recent immunohistochemical studies have indicated that NF-κB is present in the nuclei, and hence active, in the cells comprising rheumatoid synovium. Furthermore, NF-κB has been shown to be activated in human synovial cells in response to stimulation with TNF-α. Such a distribution may be the underlying mechanism for the increased cytokine and eicosanoid production characteristic of this tissue. See Roshak, A. K., et al., *J. Biol. Chem.*, 271, 31496–31501 (1996).

The NF-κB/Rel and IκB proteins are also likely to play a key role in neoplastic transformation. Family members are associated with cell transformation in vitro and in vivo as a result of overexpression, gene amplification, gene rearrangements or translocations. In addition, rearrangement and/or amplification of the genes encoding these proteins are seen in 20–25% of certain human lymphoid tumors. In addition, a role for NF-κB in the regulation of apoptosis has been reported stregthening the role of this transcription factor in the control of cell proliferation.

Several NF-κB inhibitors are described in C. Wahl, et al. *J. Clin. Invest.* 101(5), 1163–1174 (1998), R. W. Sullivan, et al. *J. Med. Chem.* 41, 413–419 (1998), J. W. Pierce, et al. *J. Biol. Chem.* 272, 21096–21103 (1997)

The marine natural product hymenialdisine is known to inhibit NF-κB. Roshak, A., et al., *JPET*, 283, 955–961 (1997). Breton, J. J and Chabot-Fletcher, M. C., *JPET*, 282, 459–466 (1997).

Salicylanilides are known compounds. A general solution preparation of salicyanilides is described by M. T. Clark, R. A. Coburn. R. T. Evans, R. J. Genco, *J. Med. Chem.*, 1986, 29, 25–29.

We have now discovered a novel method of inhibiting, the activation transcription factor NF-κB using salicylanilides.

SUMMARY OF THE INVENTION

An object of the present invention is to provide a method for treating diseases which may be therapeutically modified by altering the activity of transcription factor NF-κB.

Accordingly, in the first aspect, this invention provides a pharmaceutical composition comprising a compound according to Formula I.

In still another aspect, this invention provides a method of treating diseases in which the disease pathology may be therapeutically modified by inhibiting NFκB.

In a particular aspect, this invention provides methods for treating a variety of diseases associated with NF-κB activation including inflammatory disorders; particularly rheumatoid arthritis, inflammatory bowel disease, and asthma; dermatosis, including psoriasis and atopic dermatitis; autoimmune diseases; tissue and organ rejection; Alzheimer's disease; stroke; atherosclerosis; restenosis; cancer, including Hodgkins disease; and certain viral infections, including AIDS; osteoarthritis; osteoporosis; and Ataxia Telangiestasia.

DETAILED DESCRIPTION OF THE INVENTION

The present invention provides a method of treatment of diseases associated with NF-κB activation, comprising administering to an animal, particularly a mammal, most particularly a human in need thereof a compound of Formula I:

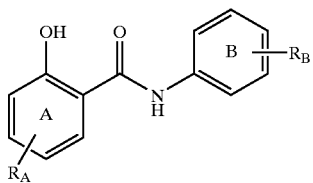

wherein:
- $R_A$ substitutes ring A 0–3 times and is independently selected from the group consisting of: $NO_2$, halogen, $C_{1-6}$alkyl, trifluoromethyl. $O-C_{1-6}$alkyl and $S-C_{1-6}$alkyl; and
- $R_B$ substitutes ring B 0–3 times and is independently selected from the group consisting of: halogen, $C(O)C_{1-6}$alkyl, $C_{1-6}$alkyl, $O—C_{1-6}$alkyl. $S—C_{1-6}$alkyl, $CH_2$-aryl, and aryl;

and pharmaceutically acceptable salts, hydrates and solvates thereof.

The present invention further provides a preferred method of treatment of diseases associated with NF-κB activation, comprising administering to an animal, particularly a mammal, most particularly a human in need thereof a compound of Formula II:

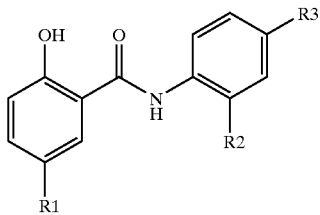

wherein $R_A$ of Formula I occurs once and is $R_1$; and $R_B$ of Formula I occurs twice and is independently $R_2$ and $R_3$. More specifically:
- $R_1$ is selected from the group consisting of: H, $NO_2$, $CF_3$, F, Cl, Br, and I;
- $R_2$ is selected from the group consisting of: H and F; and
- $R_3$ is selected from the group consisting of: F, Cl, Br, I, phenyl and $C(O)C_{1-6}$alkyl, preferably $C_{1-6}$alkyl is $CH_3$;

and pharmaceutically acceptable salts, hydrates and solvates thereof.

Compounds of Formula II selected from the following group are most preferred for use in the methods of the present invention:

N-(4-phenyl-phenyl)-2-hydroxy-5-trifluoromethylcarboxamide;

N-(2,4-Difluorophenyl)-2-hydroxy-5-nitrocarboxamide;

N-(2,4-Difluorophenyl)-2-hydroxy-5-iodocarboxamide, and

N-(4-acetylphenyl)-2-hydroxy-5-iodocarboxamide.

Definitions

The present invention includes all hydrates, solvates, complexes and prodrugs of the compounds of this invention. Prodrugs are any covalently bonded compounds which release the active parent drug according to Formulas I and II in vivo. If a chiral center or another form of an isomeric center is present in a compound of the present invention, all forms of such isomer or isomers, including enantiomers and diastereomers, are intended to be covered herein. Inventive compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention. In cases wherein compounds may exist in tautomeric forms, such as keto-enol tautomers, each tautomeric form is contemplated as being included within this invention whether existing in equilibrium or predominantly in one form.

The meaning of any substituent at any one occurrence in Formula I or any subformula thereof is independent of its meaning, or any other substituent's meaning, at any other occurrence, unless specified otherwise.

"$C_{1-6}$alkyl" as applied herein is meant to include substituted and unsubstituted methyl, ethyl, n-propyl, isopropyl, n-butyl, isobutyl and t-butyl, pentyl, n-pentyl, isopentyl, neopentyl and hexyl and the simple aliphatic isomers thereof. Any $C_{1-6}$alkyl group may be optionally substituted independently by one or two halogens, SR', OR',N(R')$_2$, C(O)N(R')$_2$, carbamyl or $C_{1-4}$alkyl, where R' is $C_{1-6}$alkyl.

"Halogen" as applied herein is meant to include F, Cl, Br, and I.

"Ar" or "aryl" as applied herein is meant to include phenyl or naphthyl, optionally substituted by one or more of Ph-$C_{0-6}$alkyl; Het-$C_{0-6}$alkyl; $C_{1-6}$alkoxy; Ph-$C_{0-6}$alkoxy; Het-$C_{0-6}$alkoxy; OH, $(CH_2)_{1-6}NR^4R^5$; $O(CH_2)_{1-6}NR^4R^5$; $C_{1-6}$alkyl, OR", N(R")$_2$, SR", $CF_3$, $NO_2$, CN, $CO_2R"$, CON(R"), F, Cl, Br or I; where $R^4$ and $R^5$ are H, $C_{1-6}$alkyl. Ph-$C_{0-6}$alkyl, or naphthyl-$C_{0-6}$alkyl; and R" is phenyl, naphthyl, or $C_{1-6}$alkyl.

Methods of Preparation

The compounds of the present invention may be conveniently prepared by the methods set forth in Schemes 1 & 2 below.

A general solution preparation of salicyanilides is described by M. T. Clark, R. A. Coburn, R. T. Evans, R. J. Genco; *J. Med. Chem*; 1986; 29; 25–29. These compounds may also be conveniently prepared by solid phase techniques. including in the form of a library.

General Preparation:

The general solution preparation is shown in Scheme 1 and 2. A salicylanilide is prepared by the condensation of a substituted salicylic acid with a substituted aniline in the presence of phosphorous trichloride in dry chlorobenzene (Scheme 1). A salicylanilde can also be prepared by conversion of a substituted salicylic acid to its corresponding acid chloride with thionyl chloride in toluene with catalytic DMF. The resulting salicylic acid chloride and a substituted aniline is then heated in toluene to form a salicyanilide (Scheme 2).

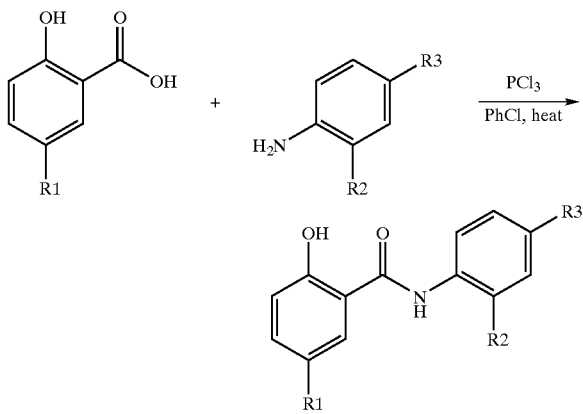

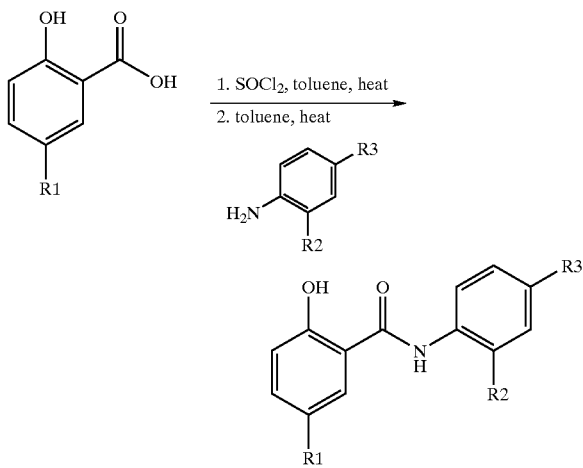

Referring to the methods of preparing the compounds of Formula I set forth in Schemes 1 & 2 above, the skilled artisan will appreciate that the present invention includes all novel intermediates required to make the compounds of Formula I.

The starting materials used herein are commercially available or are prepared by routine methods well known to those of ordinary skill in the art and can be found in standard reference books, such as the COMPENDIUM OF ORGANIC SYNTHETIC METHODS, Vol. I–VI (published by Wiley-Interscience).

Acid addition salts of the compounds of Formula I are prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as $Li^+$, $Na^+$, $K^+$, $Ca^{++}$, $Mg^{++}$ and $NH_4^+$ are specific examples of cations present in pharmaceutically acceptable salts. Halides, sulfate, phosphate, alkanoates (such as acetate and trifluoroacetate), benzoates, and sulfonates (such as mesylate) are examples of anions present in pharmaceutically acceptable salts.

This invention provides a pharmaceutical composition which comprises a compound according to Formula I and a pharmaceutically acceptable carrier, diluent or excipient. Accordingly, the compounds of Formula I may be used in the manufacture of a medicament. Pharmaceutical compositions of the compounds of Formula I prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insulation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in an emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients such as cocoa butter, glycerin, gelatin or polyethylene glycols and molded into a suppository.

The methods of the present invention include topical administration of the compounds of Formulas I and II. By topical administration is meant non-systemic administration, including the application of a compound of the invention externally to the epidermis, to the buccal cavity and instillation of such a compound into the ear, eye and nose, wherein the compound does not significantly enter the blood stream. By systemic administration is meant oral, intravenous, intraperitoneal and intramuscular administration. The amount of a compound of the invention (hereinafter referred to as the active ingredient) required for therapeutic or prophylactic effect upon topical administration will, of course, vary with the compound chosen, the nature and severity of the condition being treated and the animal undergoing treatment, and is ultimately at the discretion of the physician.

While it is possible for an active ingredient to be administered alone as the raw chemical, it is preferable to present it as a pharmaceutical formulation. The active ingredient may comprise, for topical administration, from 0.01 to 5.0 wt %. of the formulation.

The topical formulations of the present invention, both for veterinary and for human medical use, comprise an active ingredient together with one or more acceptable carriers therefor, and optionally any other therapeutic ingredients. The carrier must be "acceptable" in the sense of being compatible with the other ingredients of the formulation and not deleterious to the recipient thereof.

Formulations suitable for topical administration include liquid or semi-liquid preparations suitable for penetration through the skin to the site of where treatment is required such as: liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 90–100 C for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols. The formulation may incorporate any suitable surface active agent such as an anionic, cationic or non-ionic surface active agent such as sorbitan esters or polyoxyethylene derivatives thereof. Suspending agents such as natural gums, cellulose derivatives or in organic materials such as silicaceous silicas, and other ingredients such as lanolin, may also be included.

Utility of the Present Invention

The compounds of Formulas I and II are useful as inhibitors of NF-κB. The present invention provides useful compositions and formulations of said compounds, including pharmaceutical compositions and formulations of said compounds.

The present invention also provides methods of treatment of diseases associated with NF-κB activation, which methods comprise administering to an animal, particularly a mammal, most particularly a human in need thereof a compound of Formulas I or II. The present invention particularly provides methods for treating inflammatory disorders; particularly rheumatoid arthritis, inflammatory bowel disease, and asthma; dermatosis, including psoriasis and atopic dennatitis; autoimmune diseases; tissue and organ rejection; Alzheimer's disease; stroke; atherosclerosis; restenosis; cancer, including Hodgkins disease; and certain viral infections, including AIDS; osteoarthritis; osteoporosis; and Ataxia Telangiestasia.

For acute therapy, parenteral administration of a compound of Formulas I or II is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 50 mg/kg; preferably between 0.1 and 20 mg/kg, in a manner to maintain the concentration of drug in the plasma at a concentration effective to inhibit activation of NF-κB. The compounds are administered one to four times daily at a level to achieve a total daily dose of about 0.4 to about 80 mg/kg/day. The precise amount of an inventive compound which is therapeutically effective, and the route by which such compound is best administered, is readily determined by one of ordinary skill in the art by comparing the blood level of the agent to the concentration required to have a therapeutic effect.

The compounds of Formulas I and II may also be administered orally to the patient, in a manner such that the concentration of drug is sufficient to inhibit NF-κB or to achieve any other therapeutic indication as disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

The compounds of Formulas I and II may also be administered topically to the patient, in a manner such that the concentration of drug is sufficient to inhibit NF-κB or to achieve any other therapeutic indication as disclosed herein. Typically, a pharmaceutical composition containing the compound is administered in a topical formulation of between about 0.01% to about 5% w/w.

No unacceptable toxicological effects are expected when compounds of the present invention are administered in accordance with the present invention.

The ability of the compounds described herein to inhibit the activation of NF-κB is clearly evidenced in their ability to inibit NF-κB-driven reporter gene activity (see Table 1). The utility of the present NF-κB inhibitors in the therapy of diseases is premised on the importance of NF-κB activation in a variety of diseases.

TABLE 1

Inhibition of NF-κB-driven Reporter Gene Activity

Core structure: 2-hydroxy-benzamide with R' and R'' substituents on the ring, and N-X amide substituent.

| Compound Number | R' | R'' | X | $IC_{50}$ uM |
|---|---|---|---|---|
| 1 | I | H | 4-acetylphenyl | 8.14 |
| 2 | I | H | 3,4-difluorophenyl | ~5 |
| 3 | $NO_2$ | H | 3,4-difluorophenyl | 7.20 |
| 4 | H | Ph | 4-acetylphenyl | inactive |
| 5 | Ph | H | 4-acetylphenyl | inactive |
| 6 | Br | H | 3,4-dichlorophenyl | 0.82 |
| 7 | $CF_3$ | H | 2-biphenyl | 36.5 |
| 8 | $CF_3$ | H | 4-biphenyl | 3.55 |

NFκB plays a key role in the regulated expression of a large number of pro-inflammatory mediators including cytokines such as IL-6 and IL-8 (Mukaida et al., 1990; Liberman and Baltimore, 1990; Matsusaka et al., 1993), cell adhesion molecules, such as ICAM and VCAM (Marui et al., 1993; Kawai et al., 1995; Ledebur and Parks, 1995), and inducible nitric oxide synthase (iNOS) (Xie et al., 1994; Adcock et al., 1994). (Full reference citations are at the end of this section). Such mediators are known to play a role in the recruitment of leukocytes at sites of inflammation and in the case of iNOS, may lead to organ destruction in some inflammatory and autoimmune diseases (McCartney-Francis et al., 1993; Kleemann et al., 1993). Importantly, the compounds described herein inhibit IL-8 synthesis and the production of nitric oxide, a product of iNOS activity (see Table 2).

TABLE 2

Anti-inflammatory Activity of Compound 3 in Table 1

| In vitro | |
|---|---|
| TNF-stimulated IL-8 production in U937 cells | $IC_{50}$ = 3 uM |
| IL-1-induced PGE2 production in RSF | $IC_{50}$ = 3 uM |
| IL-1-stimulated Nitric Oxide production | $IC_{50}$ = 5 uM |
| In vivo Phorbol-ester-induced ear inflammation | |
| Ear swelling | $ED_{50}$ = 0.2 mg/ear |
| Inflammatory cell infiltration | $ED_{90}$ = 0.2 mg/ear |

Evidence for an important role of NF-κB in inflammatory disorders is obtained in studies of asthmatic patients. Bronchial biopsies taken from mild atopic asthmatics show significant increases in the number of cells in the submucosa staining for activated NFκB, total NF-κB, and NF-κB-regulated cytokines such as GM-CSF and TNFα compared to biopsies from normal non-atopic controls (Wilson et al., 1998). Furthermore, the percentage of vessels expressing NF-κB immunoreactivity is increased as is IL-8 immunoreactivity in the epithelium of the biopsy specimens (Wilson et al., 1998). As such, inhibition of IL-8 production through the inhibition of NFκB, as has been demonstrated by these compounds would be predicted be beneficial in airway inflammation.

Recent studies suggest that NF-κB may also play a critical role in the pathogenesis of inflammatory bowel disease (IBD). Activated NF-κB is seen in colonic biopsy specimens from Chron's disease and ulcerative colitis patients (Ardite et al., 1998; Rogler et al., 1998; Schreiber et al., 1998). Activation is evident in the inflamed mucosa but not in uninflamed mucosa (Ardite et al., 1998; Rogler et al., 1998) and is associated with increased IL-8 mRNA expression in the same sites (Ardite et al., 1998). Furthermore, corticosteroid treatment strongly inhibits intestinal NF-κB activation and reduces colonic inflammation (Ardite et al., 1998; Schreiber et al., 1998). Again, inhibition of IL-8 production through the inhibition of NF-κB, as has been demonstrated by these compounds would be predicted be beneficial in inflammatory bowel disease.

Animal models of gastrointestinal inflammation provide further support for NF-κB as a key regulator of colonic inflammation. Increased NF-κB activity is observed in the lamina propria macrophages in 2,4,6,-trinitrobenzene sulfonic acid (TNBS)-induced colitis in mice with p65 being, a major component of the activated complexes (Neurath et al., 1996; Neurath and Pettersson, 1997). Local administration of p65 antisense abrogates the signs of established colitis in the treated animals with no signs of toxicity (Neurath et al., 1996; Neurath and Pettersson, 1997). As such, one would predict that small molecule inhibitors of NF-κB would be useful in the treatment of IBD.

Further evidence for a role of NF-κB in inflammatory disorders comes from studies of rheumatoid synovium. Although NF-κB is normally present as an inactive cytoplasmic complex, recent immunohistochemical studies have indicated that NF-κB is present in the nuclei, and hence active, in the cellscomprising human rheumatoid synovium (Handel et al., 1995; Marok et al., 1996; Sioud et al., 1998) and in animal models of the disease (Tsao et al., 1997). The staining is associated with type A synoviocytes and vascular endothelium (Marok et al., 1996). Furthermore, constitutive activation of NF-κB is seen in cultured synoviocytes (Roshak et al., 1996; Miyazawa et al., 1998) and in synovial cell cultures stimulated with IL-1β or TNFα (Roshak et al., 1996; Fujisawa et al., 1996; Roshak et al., 1997). Thus, the activation of NF-κB may underlie the increased cytokine production and leukocyte infiltration characteristic of inflamed synovium. The ability of these compounds to inhibit NF-κB and thereby inhibit the production of eicosanoids by these cells would be predicted to yield benefit in rheumatoid arthritis (see Table 2).

Mukaida N, MaheY, Matsushima K (1990) Cooperative interaction of nuclear factor-κB-and cis-regulatory enhancer binding protein-like factor binding elements in activating the interleukin-8 gene by pro-inflammatory cytokines. *J Biol Chem* 265: 21128–21133

Liberman T A, Baltimore D (1990) Activation of interleukin-6 gene expression through NF-κB transcription factor. *Mol Cell Biol* 10: 2327–2334

Matsusaka T, Fujikawa K, Nishio Y, Mukaida N, Matsushima K, Kishimoto T, Akira S (1993) Transcription factors NF-IL6 and NF-κB synergistically activate transcription of the inflammatory cytokines interleukin 6 and interleukin 8. *Proc Natl Acad Sci USA* 90: 10193–10197

Marui N, Offerman M K, Swerlick, R, Kunsch C, Rosen C A, Ahmad M, Alexander R W, Medford RM (1993) Vascular cell adhesion molecule-1 (VCAM-1) gene transcription and expression are regulated through an antioxidant-sensitive mechanism in human vascular endothelial cells. *J Clin Invest* 92: 1866–1874

Kawai M, Nishikomori R, Jung E-Y, Tai G, Yamanak C, Mayumi M, Heike T (1995) Pyrrolidine dithiocarbamate inhibits intercellular adhesion molecule-1 biosynthesis induced by cytokines in human fibroblasts. *J Immunol* 154: 2333–2341

Ledebur H C, Parks T P (1995) Transcriptional regulation of the intracellular adhesion molecule-1 gene by inflammatory cytokines in human endothelial cells. *J Biol Chem* 270: 933–943

Xie Q, Kashiwabara Y, Nathan C (1994) Role of transcription factor NF-κB/Rel in induction of nitric oxide synthase. *J Biol Chem* 269 4705–4708

Adcock I M, Brown C R, Kwon O, Barnes P J (1994) Oxidative stress induces NF-κB DNA binding and inducible NOS mRNA in human epithelial cells. *Biochem Biophys Res Commun* 199: 518–1524

McCartney-Francis N, Allen J B, Mizel D E, Albina J E, Xie Q, Nathan C F, Wahl S M (1993) Suppression of arthritis by an inhibitor of nitric oxide synthase. *J Exp Med* 178: 749–754

Kleemann R, Rothe H, Kolb-Bachofen V, Xie Q, Nathan C, Martin S, Kolb H (1993) Transcription and translation of inducible nitric oxide synthase in the pancreas of prediabetic BB rats. *FEBS Lett* 328: 9–12

Wilson S J, Wallin A, Sandstrom T, Howarth P H, Holgate S T (1998) The expression of NF-kappa-B and associated adhesion molecules in mild asthmatics and normal controls. *J Allergy Clin Immunol* 101: 616

Ardite E, Panes J, Miranda M, Salas A, Elizalde J I, Sans M, Arce Y, Bordas J M, Femandez-Checa J C, Pique J M (1998) Effects of steroid treatment on activation of nuclear factor κB in patients with inflammatory bowel disease. *Br J Phannacol* 124:431–433

Rogler G, Brand K, Vogl D, Page S, Hofmeister R, Andus T, Knuechel R, Baeuerle P A, Scholmerich J, Gross V (1998) Nuclear factor κB is activated in macrophage and epithelial cells of inflamed intestinal mucosa. *Gastroenterol* 115:357–369

Schreiber S, Nikolaus S, Hampe J (1998) Activation of nuclear factor κB in inflammatory bowel disease. *Gut* 42: 477–484

Neurath M F, Pettersson S, Meyer zum Buschenfelde K-H, Strober W (1996) Local administration of antisense phosphorothioate oligonucleotides to the p65 subunit of NF-κB abrogates established experimental colitis in mice. *Nature Med* 2: 998–1004

Neurath M F, Pettersson S (1997) Predominant role of NF-κB p65 in the pathogenesis of chronic intestinal inflammation. *Immunobiol* 198: 91–98

Handel M L, McMorrow L B, Gravallese E M (1995) Nuclear factor-κB in rheumatoid synovium; localization of p50 and p65. *Arthritis Rheumatism* 38: 1762–1770

Marok R, Winyard P G, Coumbe A, Kus M L, Gaffney K, Blades S, Mapp P I, Morris C J, Blake D R, Kaltschmidt C, Baeuerle P A (1996) Activation of the transcription factor nuclear factor-κB in human inflamed synovial tissue. *Arthritis Rheumatism* 39: 583–591

Sioud M, Mellbye O, Forre O (1998) Analysis of the NF-κB p65 subunit, Fas antigen, Fas ligand and Bcl-2-related proteins in the synovium of RA and polyarticular JRA. *Clin ExpRheumatol* 16: 125–134

Tsao P W, Suzuki T, Totsuka R, Murata T, Takagi T, Ohmachi Y, Fujimura H, Takata I (1997) The effect of dexamethasone on the expression of activated NF-κB in adjuvant arthritis. *Clin Immunol Immunopathol* 83: 173–178

Roshak A K, Jackson J R, McGough K, Chabot-Fletcher M, Mochan E, Marshall L (1996) Manipulation of distinct NFκB proteins alters interleukin-1β-induced human rheumatoid synovial fibroblast prostaglandin E2 formation. *J Biol Chem* 271: 31496–31501

Miyazawa K, Mori A, Yamamoto K, Okudaira H (1998) Constitutive transcription of the human interleukin-6 gene by rheumatoid synoviocytes; spontaneous activation of NF-κB and CBF1. *Am J Pathol* 152, 793–803

Fujisawa K, Aono H, Hasunuma T, Yamamoto K, Mita S, Nishiola K (1996) Activation of transcription factor NF-κB in human synovial cells in response to tumor necrosis factor α. *Arthritis Rheumatism* 39: 197–203

Roshak A K, Jackson J R, Chabot-Fletcher M, Marshall L (1997) Inhibition of NFκB-mediated interleukin-1β-stimulated prostaglandin E2 formation by the marine natural product hymenialdisine. *J Pharmacol Exp Therapeut* 283: 955–961

Biological Assays

The compounds of this invention may be tested in one of several biological assays to determine the concentration of compound which is required to have a given pharmacological effect.

Assays of NF-κB activity are conducted using a cell based luciferase reporter assay as described in Breton, J. J and Chabot-Fletcher, M. C. *JPET*, 282, 459–466 (1997). Briefly, U937 human histiocytic lymphoma cell line permanently transfected with the NF-κB reporter plasmids (see below) are cultured in the above medium with the addition of 250 μg/ml Geneticin (G418 sulfate, Life Technologies, Grand Island, N.Y.). The luciferase reporter assay is conducted in the transfected U937 clones. These are twice centrifuged at 300×g for 5 min and resuspended in RPMI 1640 with 10%

FBS to a density of $1 \times 10^6$ cells/ml. One ml aliquots are added to the wells of 24-well plates. Compound or dimethyl sulfoxide (DMSO) carrier (1 μl) is added to the appropriate wells and the plates are incubated at 37° C., 5% $CO_2$ for 30 min. The stimulus is added (5 ng/ml TNFα, 100 ng/ml LPS, or 0.1 μM PMA) and the samples incubated for 5 hours at 37° C., 5% $CO_2$, transferred to 1.9 ml polypropylene tubes, and centrifuged at 200×g for 5 min. The cell pellets are washed twice in 1 ml PBS without $Ca^{2+}$ and $Mg^{2+}$, and centrifuged as indicated above. The resulting cell pellets are lysed in 50 μl 1× lysis buffer (Promega Corporation, Madison, Wis.), vortexed and incubated for 15 min at room temperature. A 20 μl aliquot of each lysate is transferred to an opaque white 96-well plate (Wallac Inc., Gaithersburg, Md.) and assayed for luciferase production in a MicroLumat LB 96 P luminometer (EG&G Berthold, Bad Wilbad, Germany). The luminometer dispenses 100 μl luciferase assay reagent (Promega Corporation, Madison, Wis.) into each well and the integrated light output is recorded for 20 sec. Light output is measured in relative light units (RLUs).

NF-κB activity may also be measured in an electrophoretic mobility shift assay (EMSA) to assess the presence of NF-κB protein in the nucleus. The cells of interest are cultured to a density of $1 \times 10^6$/ml. The cells are harvested by centrifugation, washed in PBS without $Ca^{2+}$ and $Mg^{2+}$ and resuspended in PBS with $Ca^{2+}$ and $Mg^{2+}$ at $1 \times 10^7$ cells/ml. To examine the effect of compound on the activation of NF-κB, the cell suspensions are treated with various concentrations of drug or vehicle (DMSO, 0.1%) for 30 min at 37° C. prior to stimulation with TNFα (5.0 ng/ml) for an additional 15 min. Cellular and nuclear extracts are prepared follows Briefly, at the end of the incubation period the cells ($1 \times 10^7$ cells) are washed 2× in PBS without $Ca^{2+}$ and $Mg^{2+}$. The resulting cell pellets are resuspended in 20 μl of Buffer A (10 mM Hepes (pH 7.9), 10 mM KCl, 1.5 mM $MgCl_2$, 0.5 mM dithiothreitol (DTT) and 0.1% NP-40) and incubated on ice for 10 min. The nuclei are pelleted by microcentrifugation at 3500 rpm for 10 min at 4° C. The resulting supernatant was collected as the cellular extract and the nuclear pellet was resuspended in 15 μl Buffer C (20 mM Hepes (pH 7.9), 0.42M NaCl, 1.5 mM $MgCl_2$, 25% glycerol, 0.2 mM EDTA, 0.5 mM DTT, and 0.5 mM phenylmethylsulphonyl fluoride (PMSF)). The suspensions are mixed gently for 20 min at 4° C. then microcentrifuged at 14,000 rpm for 10 min at 4° C. The supernatant is collected and diluted to 60 μl with Buffer D (20 mM Hepes (pH 7.9), 50 mM KCl, 20% glycerol, 0.2 mM EDTA, 0.5 mM DTT, and 0.5 mM PMSF). All samples are stored at −80° C. until analyzed. The protein concentration of the extracts is determined according to the method of Bradford (Bradford. 1976) with BioRad reagents.

The effect of compounds on transcription factor activation is assessed in an electrophoretic mobility shift assay (EMSA) using nuclear extracts from treated cells as described above. The double stranded NF-κB consensus oligonucleotides (5'-AGTTGAGGGGACTTTCCCAGGC-3') are labelled with $T_4$ polynucleotide kinase and [g-$^{32}$P] ATP. The binding mixture (25 μl) contains 10 mM Hepes-NaOH (pH 7.9), 4 mM Tris-HCl (pH 7.9), 60 mM KCl, 1 mM EDTA, 1 mM dithiothreitol, 10% glycerol, 0.3 mg/ml bovine serum albumin, and 1 μg poly(dI-dC)•poly(dI-dC). The binding mixtures (10 μg nuclear extract protein) are incubated for 20 min at room temperature with 0.5 ng of $^{32}$P-labelled oligonucleotide (50,000–100,000 cpm) in the presence or absence of unlabeled competitor after which the mixture is loaded on a 4% polyacrylamide gel prepared in 1×Tris borate/EDTA and electrophoresed at 200 V for 2 h. Following electrophoresis the gels are dried and exposed to film for detection of the binding reaction.

The effect of compounds on the phosphorylation of IκB may be monitored in a Western blot. Cellular extracts are subjected to sodium dodecyl sulfate-polyacrylamide gel electrophoresis (SDS-PAGE) on 10% gels (BioRad, Hercules, Calif.) and the proteins transferred to nitrocellulose sheets (Hybond™-ECL, Amersham Corp., Arlington Heights, Ill.). Immunoblot assays are performed using a polyclonal rabbit antibody directed against IκBα or IκBβ followed with a peroxidase-conjugated donkey anti-rabbit secondary antibody (Amersham Corp., Arlington Heights, Ill.). Immunoreactive bands are detected using the Enchanced Chemiluminescence (ECL) assay system (Amersham Corp., Arlington Heights, Ill.).

Effects on eicosanoid production by human synovial fibroblasts (RSF) are assessed using primary cultures of human RSF. These are obtained by enzymatic digestion of synovium obtained from adult patients with rheumatoid. Cells are cultured in Earl's Minimal Essential Medium (EMEM) containing 10% fetal bovine serum (FBS), 100 units/ml penicillin and 100 μg/ml streptomycin (GIBCO, Grand Island, N.Y.), at 37° C. and 5% $CO_2$. Cultures are used at passages 4 through 9 in order to obtain a more uniform type I fibroblast population. For some studies, fibroblasts are plated at $5 \times 10^4$ cells/ml in 16 mm (diameter) 24 well plates (Costar, Cambridge, Mass.). Cells are exposed to an optimal dose of IL-1β (1 ng/ml; Roshak et al. 1996a) (Genzyme. Cambridge, Mass.) for the designated time. Drugs in DMSO vehicle (1%) are added to the cell cultures 15 minutes prior to the addition of IL-1. Prostaglandin $E_2$ levels in cell-free medium collected at the termination of the culture period are directly measured using enzyme immunoassay (EIA) kits purchased from Cayman Chemical Co. (Ann Arbor, Mich.). Sample or standard dilutions are made with experimental medium.

Anti-inflammatory activity in vivo is assessed using the phorbol ester-induced ear inflammation model in mice. Phorbol myristate acetate (PMA) (4 μg/20 μl acetone) is applied to the inner and outer surfaces of the left ear of Male Balb/c mice (6/group) (Charles River Breeding Laboratories, Wilmington, Mass.). Four hours later, compound dissolved in 25 μl acetone is applied to the same ear. The thickness of both ears is measured with a dial micrometer (Mitutoyo, Japan) after 20 hours and a second topical dose of compound is applied. Twenty-four hours later, ear thickness measurements are taken and the data expressed as the change in thickness ($\times 10^{-3}$ cm) between treated and untreated ears. The inflamed left ears are then removed and stored at −70° until assayed for myeloperoxidase (MPO) activity, a measure of inflammatory cell infiltration.

Inflammatory cell infiltration is assessed through the measurement of myeloperoxidase activity present in the inflamed ear tissue. Partially thawed ear tissues are minced and then homogenized (10% w/v) with a Tissumizer homogenizer (Tekmar Co., Cincinnati, Ohio) in 50 mM phosphate buffer (pH 6) containing 0.5% HTAB. The tissue homogenates are taken through three cycles of freeze-thaw, followed by brief sonication (10s). MPO activity in the homogenates is determined as follows. The appearance of colored product from the MPO-dependent reaction of o-dianisidine (0.167 mg/ml, Sigma Chemical, St. Louis, Mo.) and hydrogen peroxide (0.0005%) is measured spectrophotometrically at 460 nm. Supernatant MPO activity is quantified kinetically (change in absorbance measured over 3 min, sampled at 15 s intervals) using a Beckman DU-7 spectrophotometer and a kinetics analysis package (Beckman Instruments, Inc., Sommerset, N.J.). One unit of MPO activity is defined as that degrading one micromole of peroxide per minute at 25° C.

Effects on inflammation-mediated cartilage breakdown is measured in an in vitro cartilage explant system. In this model bovine articular cartilage explants are incubated for 4 days/96 hours with or without rHuIL-1 alpha to stimulate cartilage breakdown in the presence or absence of test compound. The supernatants are removed for the nitric oxide assays. Nitric oxide was measured using the Greiss reaction and read spectrophotometrically at 530 nm. This reaction measures nitrite ($NO_2$) which is the stable end product of nitric oxide.

General

Nuclear magnetic resonance spectra were recorded at either 250, 300 or 400 MHz using, respectively, a Bruker AM 250, Bruker ARX 300 or Bruker AC 400 spectrometer. $CDCl_3$ is deuteriochloroform, $DMSO-d_6$ is hexadeuteriodimethylsulfoxide, and $CD_3OD$ is tetradeuteriomethanol. Chemical shifts are reported in parts per million (d) downfield from the internal standard tetramethylsilane. Abbreviations for NMR data are as follows: s=singlet, d=doublet, t=triplet, q=quartet, m=multiplet, dd =doublet of doublets, dt=doublet of triplets, app=apparent, br=broad. J indicates the NMR coupling constant measured in Hertz. Continuous wave infrared (IR) spectra were recorded on a Perkin-Elmer 683 infrared spectrometer, and Fourier transform infrared (FTIR) spectra were recorded on a Nicolet Impact 400 D infrared spectrometer. IR and FTIR spectra were recorded in transmission mode, and band positions are reported in inverse wavenumbers ($cm^{-1}$). Mass spectra were taken on either VG 70 FE, PE Syx API III, or VG ZAB HF instruments, using fast atom bombardment (FAB) or electrospray (ES) ionization techniques. Elemental analyses were obtained using a Perkin-Elmer 240C elemental analyzer. Melting points were taken on a Thomas-Hoover melting point apparatus and are uncorrected. All temperatures are reported in degrees Celsius.

Analtech Silica Gel GF and E. Merck Silica Gel 60 F-254 thin layer plates were used for thin layer chromatography. Both flash and gravity chromatography were carried out on E. Merck Kieselgel 60 (230–400 mesh) silica gel.

Where indicated, certain of the materials were purchased from the Aldrich Chemical Co., Milwaukee, Wis., TCI America, Portland, Oreg.

EXAMPLES

In the following synthetic examples, temperature is in degrees Centigrade (° C). Unless otherwise indicated, all of the starting materials were obtained from commercial sources. Without further elaboration, it is believed that one skilled in the art can, using the preceding description, utilize the present invention to its fullest extent. These Examples are given to illustrate the invention, not to limit its scope. Reference is made to the claims for what is reserved to the inventors hereunder.

Example 1

Preparation of N-(4-Acetylphenyl)-2-hydroxy-5-iodocarboxamide

A solution of iodosalicylic acid (1.9 g, 7.4 mmol) and 4-aminoacetophenone (0.97 g, 7.4 mmol) in chlorobenzene (40 mL) was treated with $PCl_3$ (0.323 mL, 3.7 mmol). The solution was heated at reflux under an argon atmosphere. After 2 h. the solution was filtered hot and the filtrate was left standing at RT. After 18 h solution was filtered and the solid was recrystallized from MeOH to give the title compound (0.095 g, 5% yield): $^1H$ NMR (400 MHz, DMSO-$d_6$) δ 2.5–2.6 (s, 3H), 6.8–8.2 (m, 7H), 10.1–10.2 (s, 1H).

Example 2

Preparation of N-(2,4-Difluorophenyl)-2-hydroxy-5-nitrophenylcarboxamide

A solution of 5-nitrosalicylic acid (1.4 g, 7.7 mmol) and 2,4-difluoroaniline (0.8 mL, 7.7 mmol) in chlorobenzene (40 mL) was treated with $PCl_3$ (0.338 mL, 3.8 mmol). The solution was heated at reflux under an argon atmosphere. After 2 h. the solution was filtered hot and the filtrate was left standing at RT. After 18 h the solution was filtered and the solid was recrystallized from MeOH to give the title compound (0.733 g, 35% yield): $^1H$ NMR (400 MHz, DMSO-$d_6$) δ 2.5–2.6 (s, 3H), 7.1–8.9 (m, 6H), 10.6–10.7 (s, 1H)

Example 3

Preparation of N-(2,4-Difluorophenyl)-2-hydroxy-5-iodophenylcarboxamide a) 5-Iodosalicylic Acidchloride 5-Iodosalicylic acid (2.0 g, 7.58 mmol) in toluene was treated with SOCl2 (1.66 mL, 22.7 mmol) and catalytic DMF at reflux for 1 h. The reaction mixture was evaporated to dryness and the acid chloride used in the next step without purification.

b) 2,4-Difluorophenyl)-2-hydroxy-5-iodophenylcarboxamide

The compound of Example 3(a) (3.79 mmol) and 2,4-difluoroaniline (380 μL, 3.79 mmol) in toluene was heated at reflux for 24 h. The reaction mixture was evaporated, the residue washed with ether and the solid residue recrystallized from MeOH to give 159 mg of N-(2,4-difluorophenyl)-2-hydroxy-5-iodophenylcarboxamide. ES MS (M+H)$^-$ m/e 373.7.

The above specification and Examples fully disclose how to make and use the compounds of the present invention. However, the present invention is not limited to the particular embodiments described hereinabove, but includes all modifications thereof within the scope of the following claims. The various references to journals, patents and other publications which are cited herein comprise the state of the art and are incorporated herein by reference as though fully set forth.

We claim:

1. A method of inhibiting NF-κB comprising administering to a patient in need of NF-κB inhibition an amount effective for inhibiting NF-κB of a compound of Formula I:

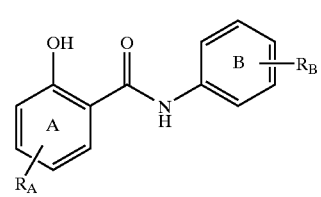

I wherein:

$R_A$ substitutes ring A 0–3 times and is independently selected from the group consisting of: $NO_2$, halogen, $C_{1-6}$alkyl, trifluoromethyl, $O—C_{1-6}$alkyl and $S—C_{1-6}$alkyl; and $R_B$ substitutes ring B 0–3 times and is independently selected from the group consisting of: halogen, C(O)

$C_{1-6}$alkyl, $C_{1-6}$alkyl, O—$C_{1-6}$alkyl, S—$C_{1-6}$alkyl, $CH_2$-aryl, and aryl;

and pharmaceutically acceptable salts, hydrates and solvates thereof.

2. A method according to claim 1 wherein:

$R_A$ occurs once and is $R_1$; and $R_B$ occurs twice and is independently $R_2$ and $R_3$.

3. A method according to claim 2 comprising administering to a patient in need thereof an effective amount of a compound of Formula II:

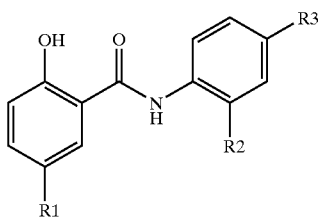

II wherein:

$R_1$ is selected from the group consisting of: H, $NO_2$, $CF_3$, F, Cl, Br, and I;

$R_2$ is selected from the group consisting of: H and F; and $R_3$ is selected from the group consisting of: F, Cl, Br, I, phenyl and $C(O)C_{1-6}$alkyl.

4. A method according to claim 3 wherein said compound is selected from the group consisting of:

N-(4-phenyl-phenyl)-2-hydroxy-5-trifluoromethylcarboxamide;

N-(2,4-Difluorophenyl)-2-hydroxy-5-nitrocarboxamide;

N-(2,4-Difluorophenyl)-2-hydroxy-5-iodocarboxamide; and

N-(4-acetylphenyl)-2-hydroxy-5-iodocarboxamide.

* * * * *